US00PP27589P3

(12) United States Plant Patent
Moon

(10) Patent No.: US PP27,589 P3
(45) Date of Patent: Jan. 24, 2017

(54) **SWEETBAY *MAGNOLIA* TREE NAMED 'MVMTF'**

(50) Latin Name: *Magnolia virginiana*
Varietal Denomination: MVMTF

(71) Applicant: SOUTHERN SELECTIONS, LLC, Loganville, GA (US)

(72) Inventor: Dwayne C. Moon, Loganville, GA (US)

(73) Assignee: Southern Selections, LLC, Logansville, GA (US)

( * ) Notice: Subject to any disclaimer, the term of this patent is extended or adjusted under 35 U.S.C. 154(b) by 150 days.

(21) Appl. No.: 14/121,906

(22) Filed: Oct. 31, 2014

(65) Prior Publication Data

US 2016/0128256 P1 May 5, 2016

(51) Int. Cl.
*A01H 5/02* (2006.01)

(52) U.S. Cl.
USPC ..... Plt./223

(58) Field of Classification Search
USPC ..... Plt./223
See application file for complete search history.

(56) References Cited

U.S. PATENT DOCUMENTS

| | | | | |
|---|---|---|---|---|
| PP12,065 | P2 * | 8/2001 | Cully | Plt./223 |
| PP12,204 | P2 * | 11/2001 | Smith | Plt./223 |
| PP17,814 | P3 * | 6/2007 | Boyd | Plt./223 |
| PP22,248 | P2 * | 11/2011 | Dirr | Plt./223 |
| PP22,694 | P2 * | 5/2012 | Hooper | Plt./223 |
| PP26,685 | P3 * | 5/2016 | Jury | Plt./223 |

OTHER PUBLICATIONS

Burncoose Nurseries, How to Care for Magnolias, p. 1-2, https://www.burncoose.co.uk/site/page.cfm?page_ref=how_to_care_for_Magnolias, downloaded Jun. 3, 2016.*

* cited by examiner

*Primary Examiner* — Anne Grunberg
(74) *Attorney, Agent, or Firm* — Stinson Leonard Street, LLP

(57) ABSTRACT

A new and distinct Sweetbay *Magnolia* tree (*Magnolia virginiana*) named 'MVMTF' having a compact habit with dense canopy, profuse flowering from May to October with small light green leaves that mature to a dark green that is true to evergreen withstanding low winter temperatures and also capable of being reproduced reliability from vegetative cuttings.

10 Drawing Sheets

Latin name of genus and species: *Magnolia virginiana.*

Varietal denomination: Sweetbay *Magnolia* tree which I have named MVMTF.

CROSS REFERENCE TO RELATED APPLICATIONS

Not applicable.

STATEMENT REGRDING FEDERALLY SPONSORED RESEARCH OR DEVELOPMENT

Not applicable.

BACKGROUND OF THE INVENTION

The present invention relates to a new and distinct variety of Sweetbay *Magnolia* tree (*Magnolia virginiana*), which I have named 'MVMTF'.

Discovery

The new *Magnolia virginiana* is a product of chance discovery. The new variety 'MVMTF' is the result of a selection made by the inventor, Dwayne Moon, from a number of *Magnolia virginiana* seedlings planted in the spring of 2008 in a production field at Moon's Tree Farm, Inc, 6327 Hwy. 20, Loganville, Ga. in Walton County. Originally the seedlings were purchased in 2006 from a nursery in Florida which takes seeds collected in the wild, sows them in seed beds, lifts them and distributes them at the end of the year as *Magnolia virginiana* bare-root seedlings. Evaluation of this tree continues in a field at Moon's Tree Farm, Inc., 175 Happy Hollow Rd, Washington, Ga. in Wilkes County.

Propagation

'MVMTF' was asexually propagated by the method of vegetative cutting at my direction in the summer of 2009 at Moon's Tree Farm in Loganville, Walton County, Ga. This propagation from softwood cuttings and resulting progeny has proven the characteristics of my new variety to be genetically stable. Furthermore, these observations have confirmed that my new variety represents a new and improved variety of Sweetbay *Magnolia* tree as particularly evidenced by the smaller habit with full canopy, medium growth rate, and small light green new growth that matures to dark green in summer and holds foliage through the winter. These genetic traits can be consistently reproduced by asexual propagation.

Uniqueness

'MVMTF' was discovered in a block of seedling Sweetbay *Magnolia* trees purchased from a supplier of liners in Florida. I claim that the genetic characteristics of this tree are the result of naturally occurring cross-pollination. Due to the nature of the seedling purchase, comparison of surrounding cross pollinators is not possible. The characteristics of my new tree distinguish it from other typical seedling Sweetbay *Magnolia* trees and the known cultivars. At the time this tree was selected, I observed 'MVMTF' Sweetbay *Magnolia* tree as a 3" caliper tree exhibiting a compact, dense canopy, profuse flowering from May to October with small light green leaves like (RHS 143D) that mature to a dark green like (RHS 137A) and which will remain evergreen throughout the winter. It also has the ability to withstand much lower winter temperatures than trees of the species. The remainder of the trees in this block had irregular structure and medium green foliage color and defoliates in winter.

Use

'MVMTF' was observed for a period of several years and is believed to be particularly useful for street tree planting and in large areas such as golf courses, commercial sites and parks. 'MVMTF' will also benefit growers who will profit from the desired look of a small native *magnolia* which has profuse flowering from May to October and which is able to hold its foliage all winter.

SUMMARY OF THE INVENTION

Background

A Sweetbay *Magnolia* tree is native to the southeastern United States north from Massachusetts to Florida, Oklahoma, Arkansas and Texas near the coast in swampy soils. It thrives in wet and even swampy soils; it tolerates shade and seems to grow best in warm climates. It requires an acid soil in this area. This species is a small, multi-stemmed, deciduous shrub of loose, open, upright spreading habit in the North with a typical height of 10 to 20 foot and 10 to 20 foot width, deciduous and evergreen. My new cultivar differs from the species in that it is asexually reproduced and has a small evergreen leaf The ultimate height and width of 'MVMTF' is not known. I expect my new variety of Sweetbay *Magnolia* tree to perform as well as the species.

Industry Representation

A cultivated Sweetbay *Magnolia* tree is predominantly represented in the industry by seedling material reproduced sexually through seed production and seedling establishment. This accounts for a high degree of variability in the industry, both in the landscape and nursery industry. Seedling Sweetbay *Magnolia* tree is variable in growth rate and habit, typically has a central leader, and tends to be open in youth. At the time of submission, the only two commercially available cultivars that I currently am aware of are *Magnolia virginiana* 'Jim Wilson' Moonglow® U.S. Plant Pat. No. 12,065 and 'Mattie Mae Smith' U.S. Plant Pat. No. 12,204 P2. 'Jim Wilson' Moonglow® has a vigorous upright growth, cold hardiness with semi-evergreen foliage in the northern part of its range, and larger than usual flowers which bloom through June. The present cultivar 'MVMTF' differs from *Magnolia virginiana* 'Jim Wilson' Moonglow® U.S. Plant Pat. No. 12,065 in that 'MVMTF' has a more vertical habit, it flowers from May to October, and it has a distinct slender foliage which is light green like (RHS 143D) in spring, dark green like (RHS 137A) in summer and will remain evergreen throughout winter. My selection in the spring of 2012 was 3" caliper measured at 6" above the ground with a height of 10' and a width of 5' giving it a 2-1 height to width ratio. *Magnolia virginiana* 'Jim Wilson' Moonglow® U.S. Plant Pat. No. 12,065 at 3" caliper measured at 6" above the ground has a height of 12' and a width of 8' giving it a 3/2 height to width ratio based on its patent description. 'Mattie Mae Smith' has a compact habit and is slow growing with a variegated-leaf selection along with flowers which bloom from late April through early May. The present cultivar 'MVMTF' differs from *Magnolia virginiana* 'Mattie Mae Smith' in that 'MVMTF' has a more vertical habit, it flowers longer from May to October while 'Mattie Mae Smith' blooms from late April through early May, and 'MVMTF' has a distinct slender foliage which is light green like (RHS 143D) in spring, dark green like (RHS 137A) in summer and will remain evergreen throughout winter while 'Mattie Mae Smith' has a variegation of its foliage. These form differences with unique foliage colors, its prolonged blooming and evergreen foliage throughout the winter make my selection uniquely different from all known patent selections and seedlings.

BRIEF DESCRIPTION OF THE DRAWINGS

The accompanying photographs depict the color of the tree and foliage of my new variety as nearly as is reasonably possible to make the same in a color illustration of this character.

FIG. 6 shows the trunk of my new variety;

DETAILED DESCRIPTION OF THE INVENTION

Botanical Description of the Plant

Figure 1:
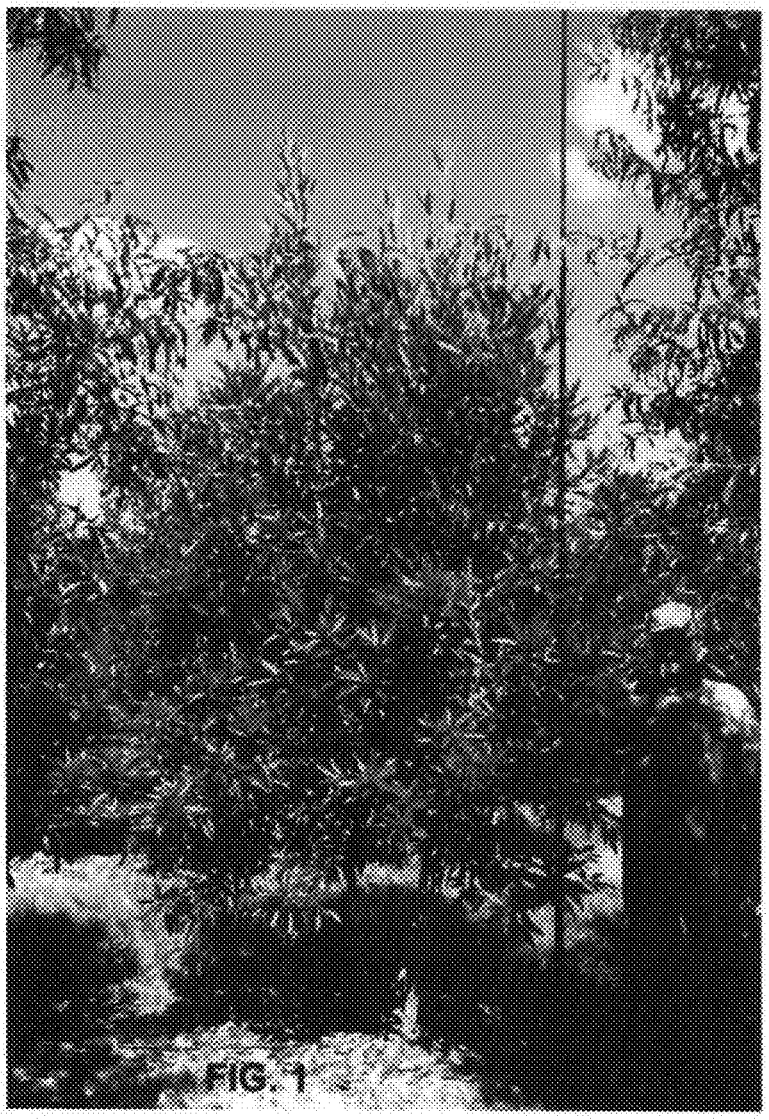
FIG. 1 taken in the production field of Walton County, Loganville, Ga. shows the initially discovered tree.
Figure 2:
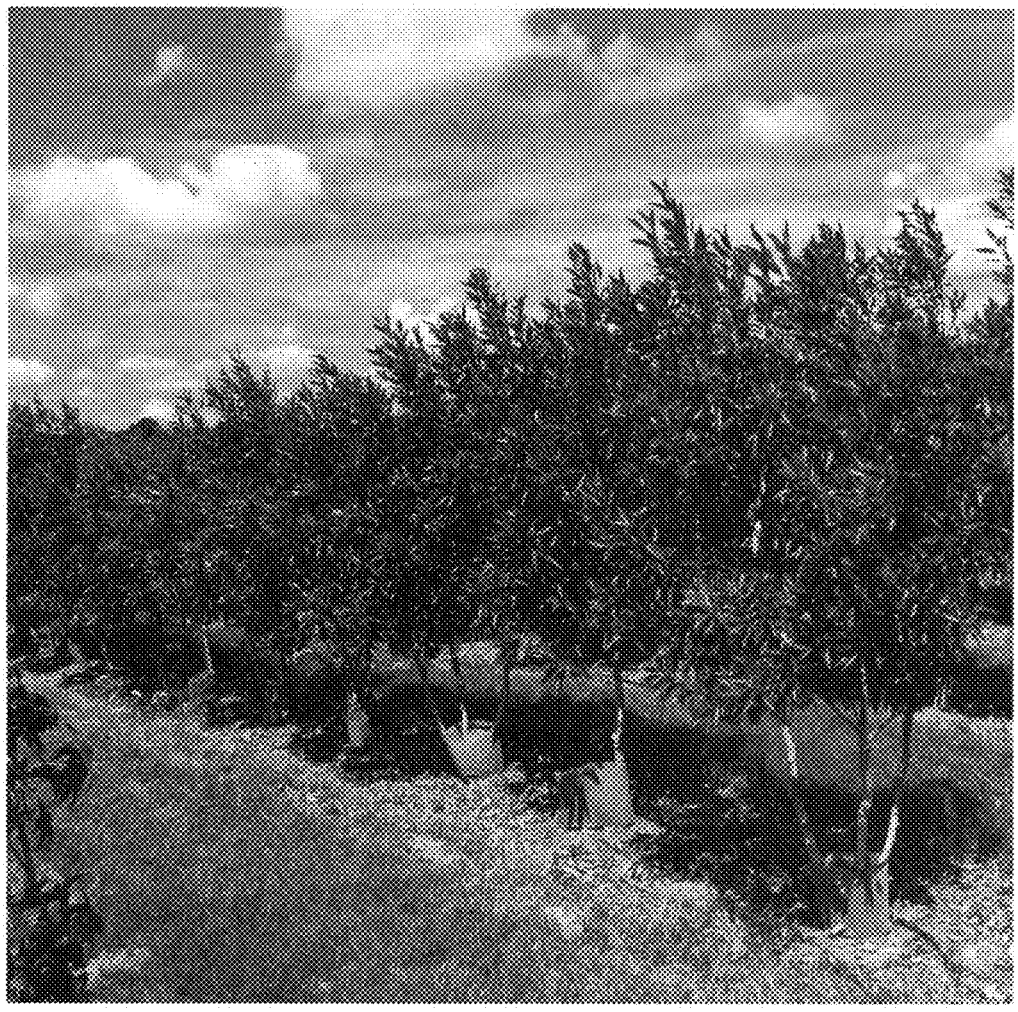
FIG. 2 taken of a field block shows the progeny of my new variety.
Figure 3:
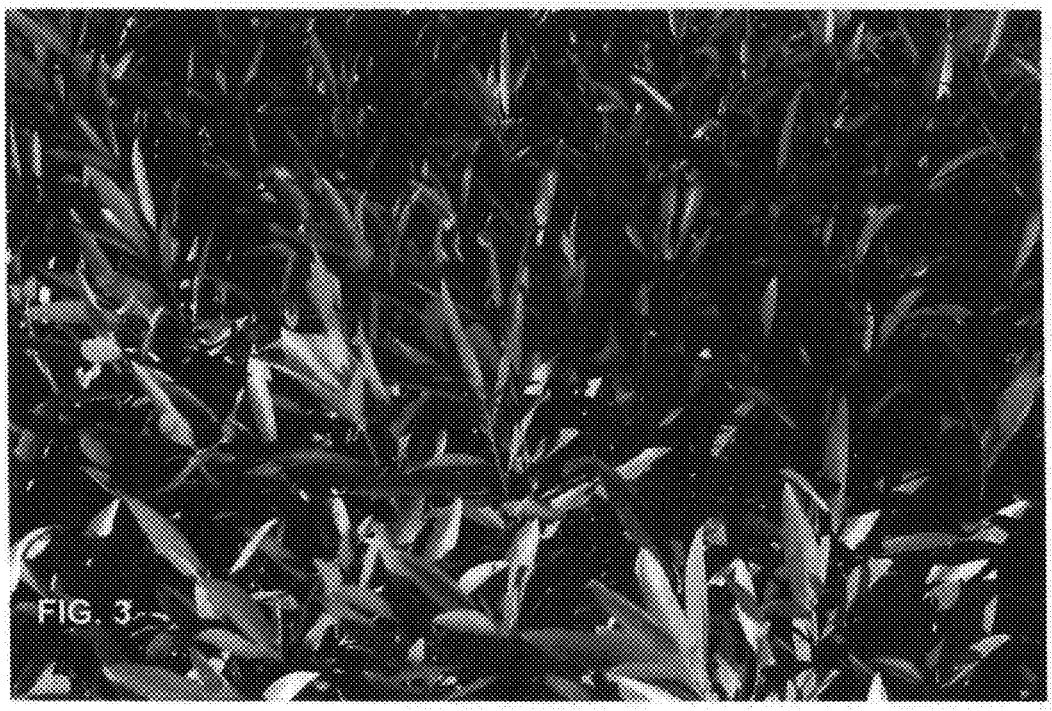
FIG. 3 shows propagation of rooted cuttings.
Figure 4:
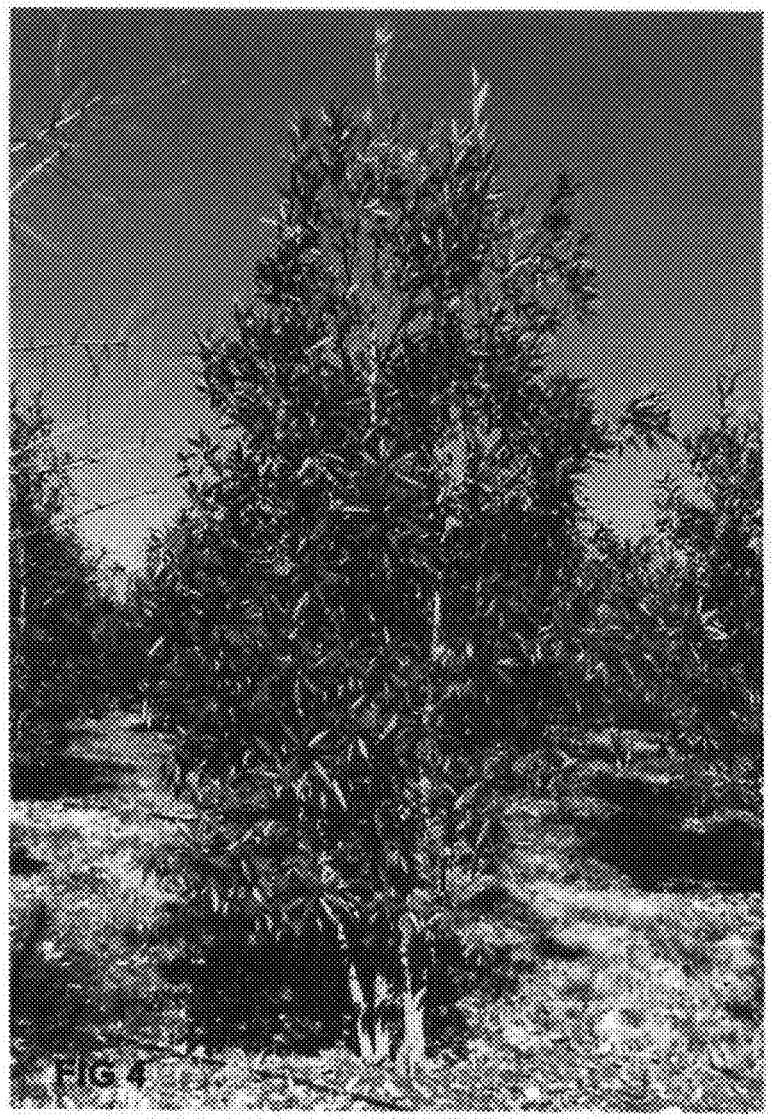
FIG. 4 taken during the February of 2014 shows my new variety in winter.
Figure 5:
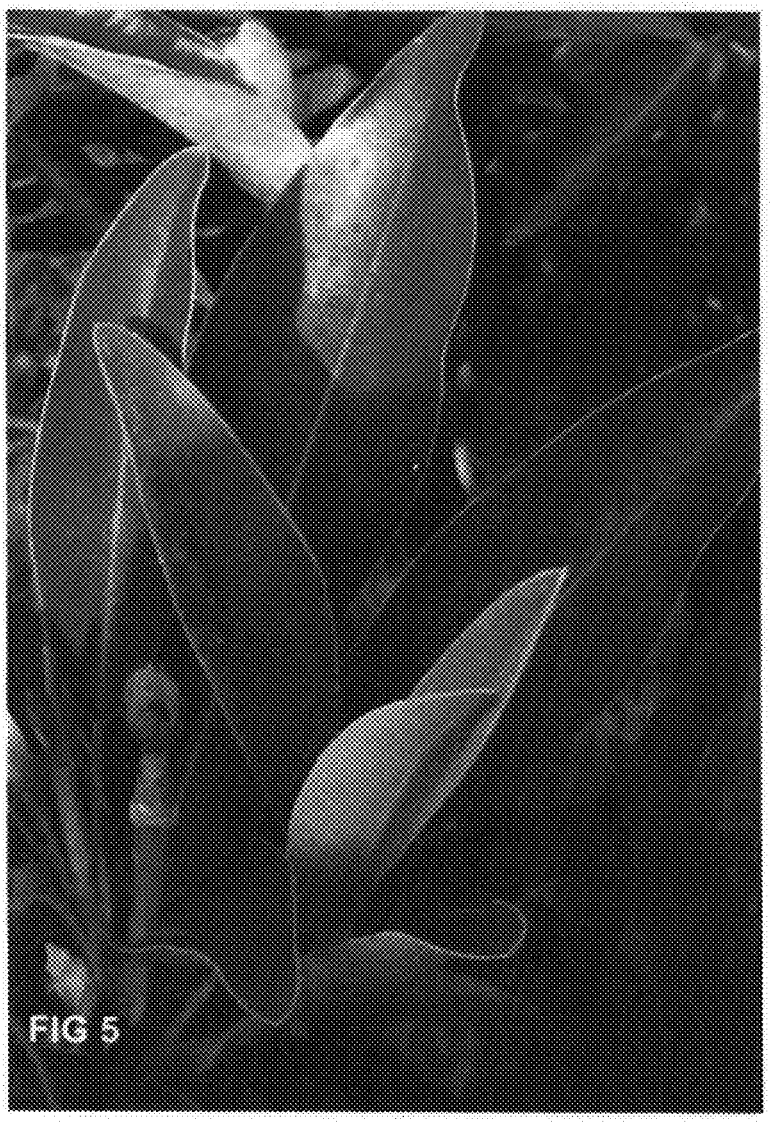
FIG. 5 shows the foliage of my new variety.
Figure 3:
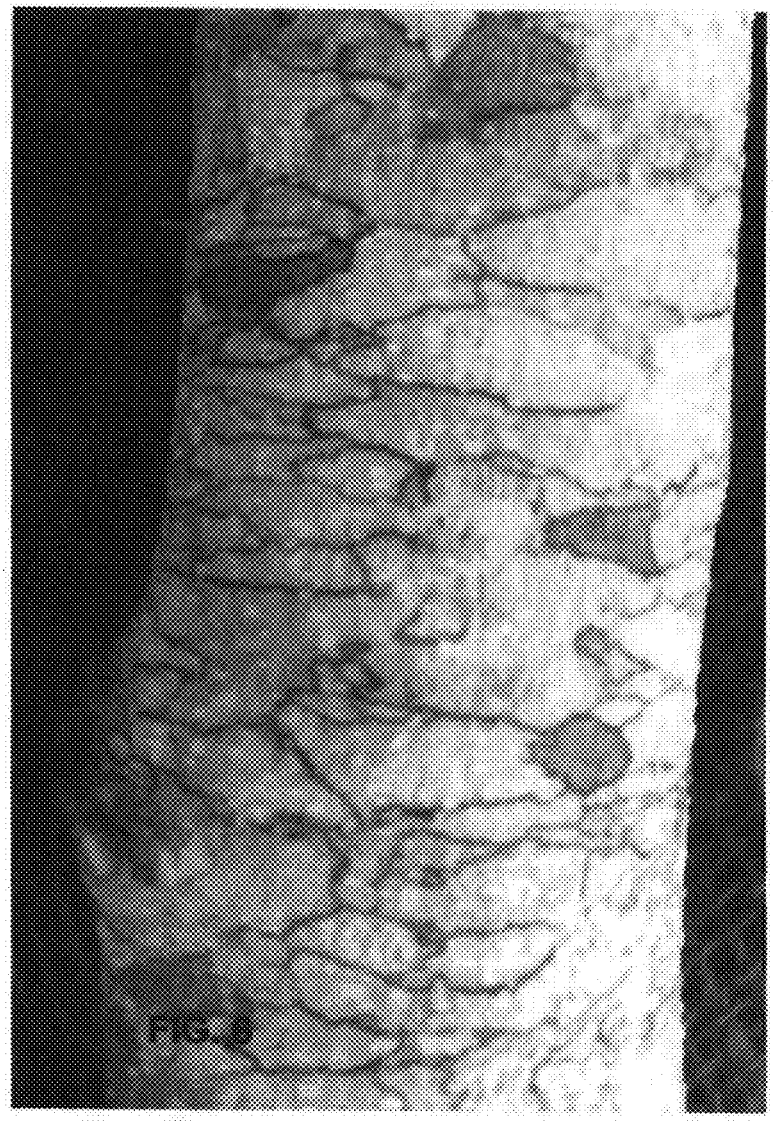
Figure 7:
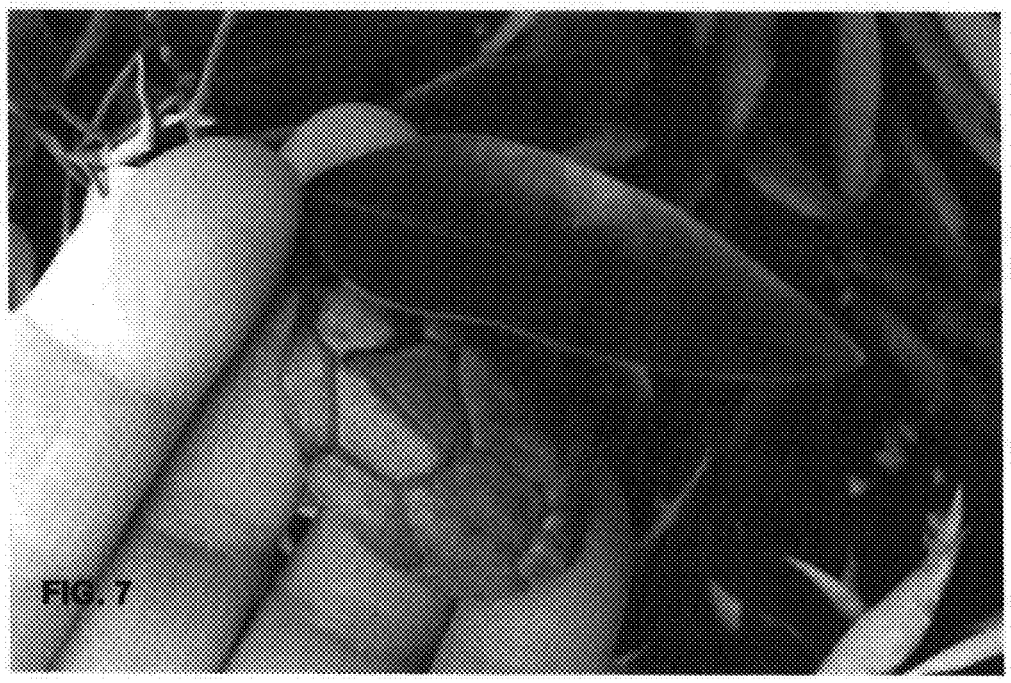
FIG. 7 shows the seed pod of my new variety.
Figure 8:
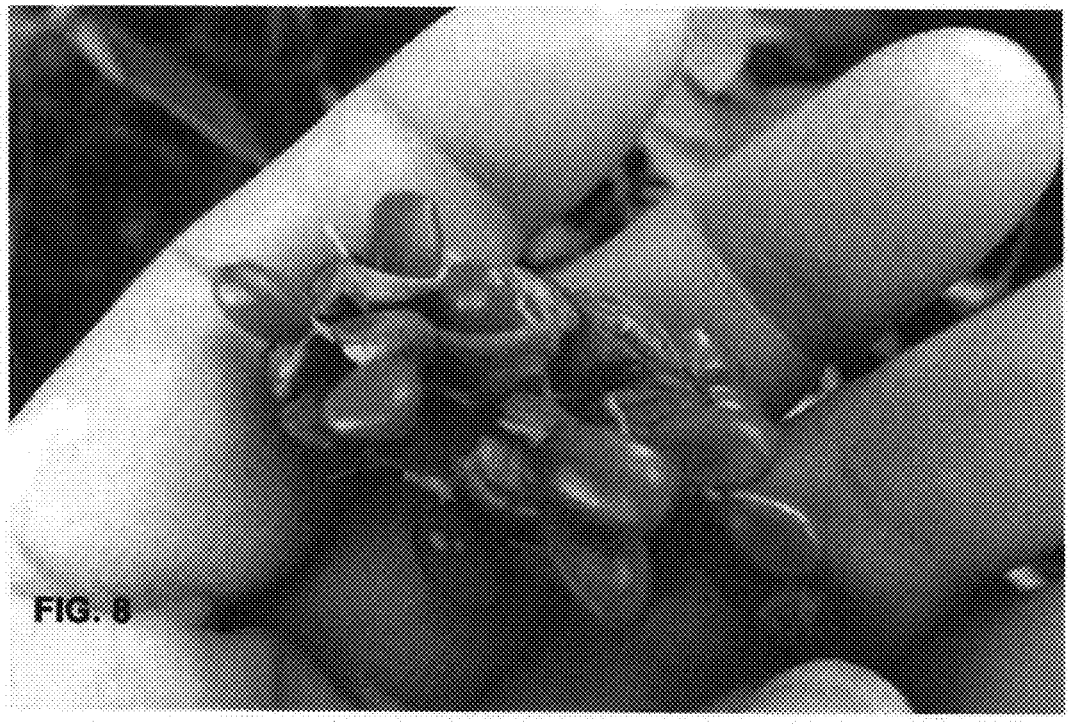
FIG. 8 shows the fruit of my new variety.
Figure 9:
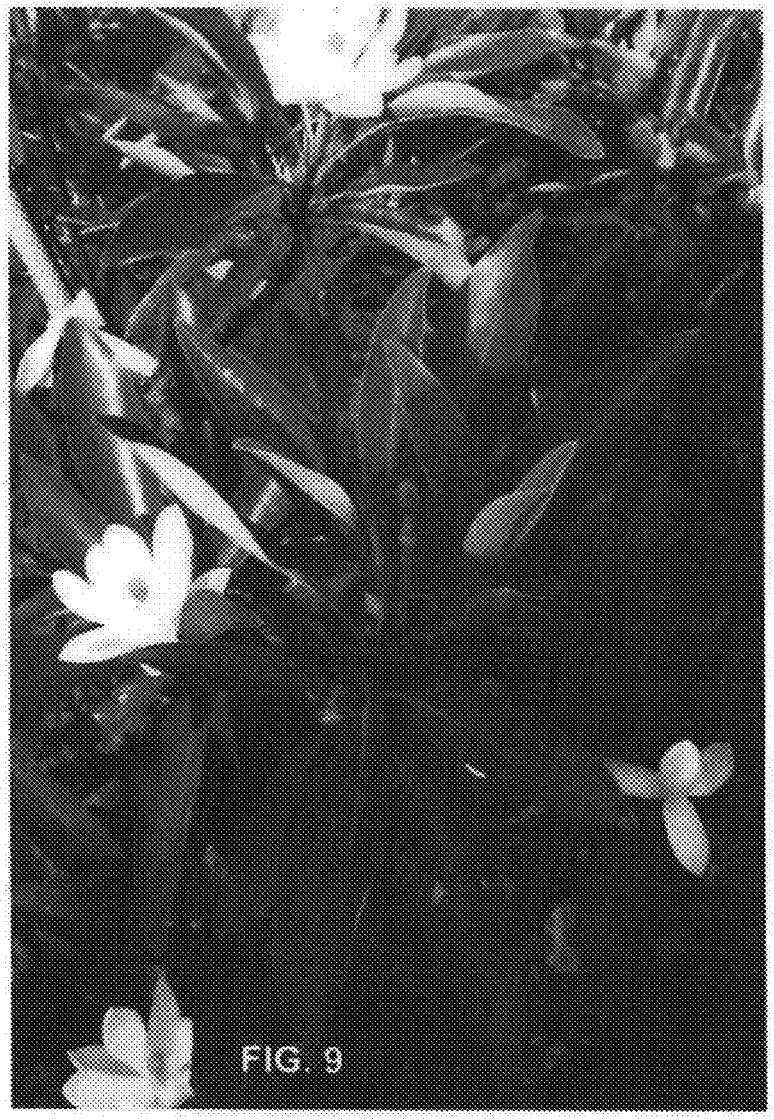
FIG. 9 shows the bloom of my new variety.
Figure 10:
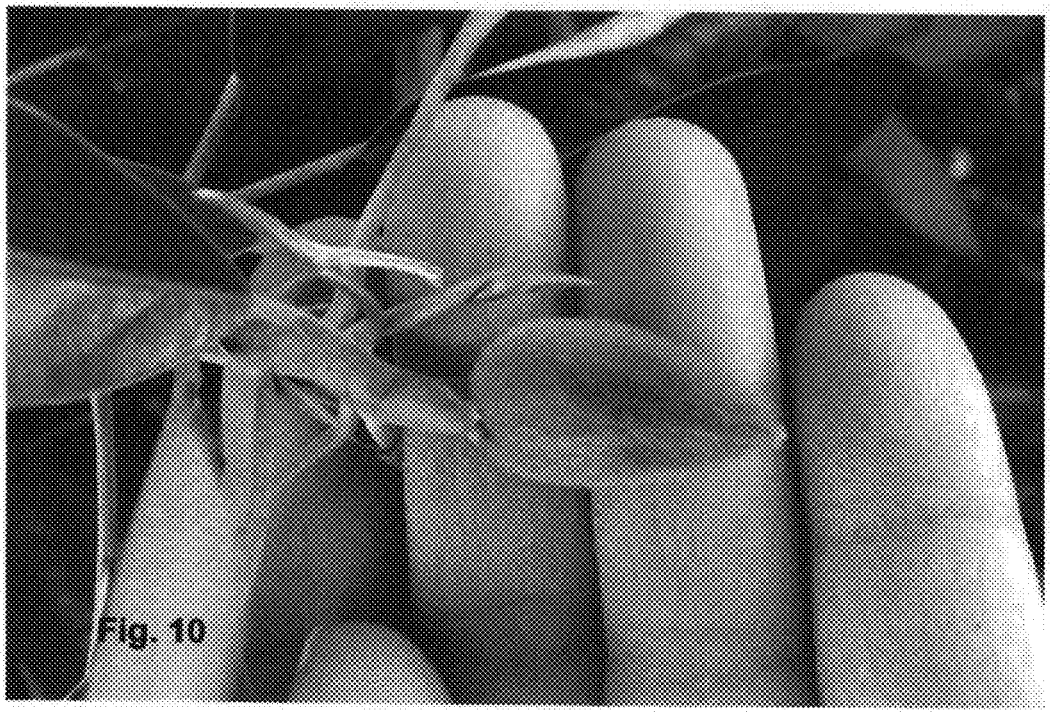
FIG. 10 shows the bud of my new variety.

The following is a detailed description of 'MVMTF' Sweetbay *Magnolia* tree with color terminology in accordance with The Royal Horticulture Society (R.H.S.) Colour Chart except where the context indicates a term having its ordinary dictionary meaning.

My new tree has not been observed under all growing conditions, and variations may occur as a result of different growing conditions. All progeny of my new variety, insofar as have been observed, have remained genetically stable in all characteristics described hereinafter. Other than as set out hereinafter, as of this time, no other characteristics have been observed which are different from common Sweetbay *Magnolia* trees, which have been observed by the inventor.

PROPAGATION

Time to initiate roots: About 15 days at 27 degrees C.

Time to produce a rooted cutting: About 60 days at 27 degrees C.

Root description: Fibrous typical of *Magnolia virginiana*.

PLANT

Growth habit: Compact, pyramidal with dense branching and dominant central leader.
Age of plant described: 3 years.
In a container or in the ground: Ground.
Height: Approximately 2.4 meters.
Plant spread: Approximately 1.2 meters.
Growth rate: Slow to average.
Length of primary lateral branches: Approximately 61 cm.
Diameter of lateral branches: Approximately 0.3 cm.
Quantity of lateral branches: Approximately 20.
Trunk:
*Diameter*.—Approximately 5 cm after 3 years. Measured at approximately 15 cm above soil level.
*Texture*.—Smooth.
*Color*.—Irregular circular splotches of Greyed-Green like (RHS 194B) to (RHS 198A).

FOLIAGE

Leaf:
*Arrangement*.—Alternate.
*Quantity*.—Approximately 8 per main branch.
*Average length*.—Approximately 10-13 cm.
*Average width*.—Approximately 3-4 cm.
*Shape of blade*.—Ovate to elliptical.
*Apex*.—Acuminate.
*Base*.—Cuneate.
*Margin*.—Entire.
*Texture of top surface*.—Smooth.
*Texture of bottom or surface*.—Smooth.
*Pubescence*.—Glabrous on both surfaces.
*Leaf internode length*.—Approximately 3 cm.
*Color*.—Young foliage upper side: Light green like (RHS 143D). Young foliage under side: Light green like (RHS 143D). Mature foliage upper side: Dark green like (RHS 137A). Mature foliage underside: Greyed-green like RHS 138B).
*Venation*.—Type: Pinnate. Venation color upper side: Yellow-green like (RHS 144D).
*Venation color under side*.—Yellow-green like (RHS 146D).
*Petiole*.—Average length: Approximately 3 cm. Color: Yellow-green like (RHS 146C).
*Diameter*.—Approximately 1 mm.

FLOWER

Natural flowering season: May to October in the Southern United States.
Begins flowering after how many years/months: 1 year from bud stage.
Inflorescence type and habit: Singly occurring, overlapping cupping flowers.
Rate of flower opening: Approximately 6 days from bud to fully opened flower.
Flower longevity on plant: 4 to 5 days after fully opened.
Quantity of flowers: Approximately 50 open flowers per tree.
Flower size:
*Diameter*.—Approximately 5-6 cm.
*Height*.—Approximately 2-3 cm.
Pedicel:
*Length*.—Approximately 1 cm.
*Diameter*.—Approximately 4 mm.
Petals:
*Petal arrangement*.—Whorled, overlapping.
*Size*.—Length: Approximately 2-3 cm. Width: Approximately 1-2 cm.
*Margin*.—Entire.
*Apex*.—Rounded.
*Petal quantity*.—12.
*Texture*.—Smooth.
Color:
*Petals*.—Upper surface: Yellow-white like (RHS 158D). Lower surface: Yellow-white like (RHS 158C).
Bud:
*Shape*.—Ovate.
*Length*.—Approximately 3 cm.
*Diameter*.—Approximately 1-2 cm.
*Color*.—Greyed-green like (RHS 195A).
Sepals/tepals:
*Shape*.—Lanceolate.
*Quantity*.—12.
*Length*.—Approximately 1 cm.
*Width*.—Approximately 0.5 cm.
*Margin*.—Entire.
*Texture*.—Smooth.
*Fragrance*.—Moderate, slightly lemony.

REPRODUCTIVE ORGANS

Staemens:
*Number*.—Approximately 35.
*Filament length*.—Approximately 1.5 cm.
*Filament color*.—Like (RHS 10A).
Anthers:
*Length*.—Approximately 0.7 cm.
*Shape*.—Linear.
*Color*.—Colored by moderately produced pollen like (RHS 20A).
Pistil:
*Number*.—1.
*Length*.—Approximately 1.5 cm.
*Style*.—Length: Approximately 1.3 cm. Color: Like (RHS 2C).

OTHER CHARACTERISICS

Fruit: Subglobose to ellipsoid, medium green like (RHS 138B) 3 cm long and 2 cm wide, cone-like aggregate with separate pointed carpels, each with two dark red seeds like (RHS 44B).
Disease/pest resistance: No disease or pests.
Temperature tolerance: The new variety is suitable for growing in USDA zones 3 through 9.

What is claimed is:

1. A new and distinct variety of Sweetbay *Magnolia* tree named 'MVMTF' substantially as herein shown, illustrated and described, characterized particularly as to novelty by its compact habit with dense canopy, profuse flowering from May to October with small light green leaves that mature to a dark green that is true to evergreen withstanding low winter temperatures and also capable of being reproduced reliability from vegetative cuttings.

* * * * *